United States Patent

Noverola et al.

[11] Patent Number: 5,223,504
[45] Date of Patent: Jun. 29, 1993

[54] XANTHINE COMPOUNDS AND COMPOSITIONS, AND METHODS OF USING THEM

[75] Inventors: Armando V. Noverola; Jose M. P. Soto; Jacinto M. Mauri; Robert W. Gristwood, all of Barcelona, Spain

[73] Assignee: Laboratorios Almirall SA, Barcelona, Spain

[21] Appl. No.: 743,388

[22] PCT Filed: Dec. 27, 1990

[86] PCT No.: PCT/GB90/02027

§ 371 Date: Aug. 16, 1991

§ 102(e) Date: Aug. 16, 1991

[87] PCT Pub. No.: WO91/09859

PCT Pub. Date: Jul. 11, 1991

[30] Foreign Application Priority Data

Dec. 27, 1989 [GB] United Kingdom ............... 8929208

[51] Int. Cl.$^5$ .................. C07D 473/08; A61K 31/52
[52] U.S. Cl. ................................. 514/263; 544/267; 544/273
[58] Field of Search ............ 544/273, 262, 266, 267; 514/263

[56] References Cited

U.S. PATENT DOCUMENTS 4,233,303 11/1980 Bergstrand et al. ............... 424/253

FOREIGN PATENT DOCUMENTS 1735    5/1979  European Pat. Off. .
1245969 8/1967  Fed. Rep. of Germany .
2831037 2/1979  Fed. Rep. of Germany .

Primary Examiner—Nicholas S. Rizzo
Attorney, Agent, or Firm—Spencer, Frank & Schneider

[57] ABSTRACT

Xanthines of the general formula:

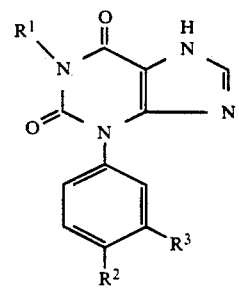

wherein $R^1$ represents a straight or branched chain alkyl, alkenyl or alkynyl group of 3-6 carbon atoms, and $R^2$ and $R^3$, which may be the same or different, each represent hydrogen or halogen or a methyl, methoxy, nitro or trifluoromethyl group or $R^2$ and $R^3$ together form a methylenedioxy or ethylenedioxy group; with the proviso that $R^2$ and $R^3$ are not both hydrogen; and pharmacologically acceptable salts thereof with an alkali metal base or a nitrogen base containing organic base, are bronchodilators making them of value in treating asthma and vasodilators making them of interest in treating angina, hypertension, congestive heart failure and multi-infarct dementia. The compounds are also of use in combatting other conditions where inhibition of PDE type IV is thought to be beneficial. The compounds can be prepared by treating and corresponding 6-amino uracil with sodium nitrite and formic acid in an excess of formamide and adding sodium dithionate to reduce the resulting 6-amino-5-nitroso compound to give the 5,6-diamino compound that ring closes with the excess of formamide.

9 Claims, No Drawings

XANTHINE COMPOUNDS AND COMPOSITIONS, AND METHODS OF USING THEM

This application is the national stage of international application PCT/GB/90/02027 filed Dec. 27th, 1990, and claims priority to British Application 8929208.0 filed Dec. 27th, 1989.

This invention relates to new therapeutically useful xanthine derivatives, to processes for their preparation and pharmaceutical compositions containing them.

It is known that cyclic adenosine monophosphate (AMP, a cyclic nucleotide) is an important mediator of cellular function, and when its intracellular concentration is increased e.g. via adenylate cyclase stimulation, effects such as smooth muscle relaxation, cardiac stimulation and inhibition of secretory cells are provoked.

The phosphodiesterases (PDE) are the enzymes responsible for the destruction of cyclic nucleotides and like stimulants of nucleotide cyclases, PDE inhibitors also increase levels of cyclic AMP and are effective as bronchodilators, vasodilators, cardiac stimulants, etc.

Many xanthine derivatives, such as theophylline, have been described as PDE inhibitors, however, its lack of selectivity against the different types of PDE is be one reason for the undesirable side effect profile seen with theophylline in man.

There are currently known to be at least 7 different types of PDE enzymes. Inhibition of PDE III (a cyclic guanosine monophosphate inhibited, high affinity cyclic adenosine monophosphate enzyme, see Reeves et al., 1987. Biochem J. 241, 535) increases intracellular cyclic adenosine monophosphate concentrations and effects include a specific cardiac stimulation. Selective inhibition of PDE IV, (a particular cyclic AMP phosphodiesterase, see Reeves et al. 1987) on the other hand increases intracellular cyclic adenosine monophosphate concentrations and produces responses associated with these increases but without directly producing cardiac stimulation. Thus selective PDE IV inhibitors are useful in the treatment of diseases in which the production of cardiac stimulation is not appropiate (e.g. asthma).

We have now unexpectedly found that xanthine derivatives with a substituted phenyl group in position 3 and a 3-6 carbon atom chain in position 1, potently inhibit type IV-PDE and are much weaker at inhibiting the type III enzyme, and for this reason they are useful in the treatment of disease without directly producing cardiac stimulation.

The new xanthine derivatives of the present invention are accordingly those compounds of the general formula:

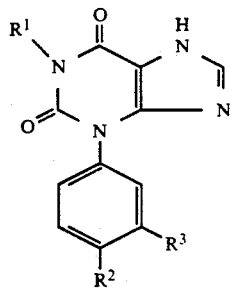

wherein R1 represents a straight or branched chain alkyl, alkenyl or alkynyl group containing from 3 to 6 (preferably or 4) carbon atoms, and R2 and R3 each represent hydrogen or halogen or a methyl, methoxy, nitro or trifluoromethyl group or R2 and R3 form together a methylenedioxy or ethylenedioxy group; with the proviso that $R^2$ and $R^3$ are not both hydrogen, and pharmacologically acceptable salts thereof formed with an alkali metal base or a nitrogen-containing organic base.

Preferred compounds of general formula I are those wherein $R^1$ a straight chain alkyl group or those wherein $R^1$ represents a n- or isopropyl, n-,iso or tert-butyl or n-hexyl group, R2 and R3 which may be the same or different represent hydrogen or halogen e.g. F, Cl or Br, or a methoxy group or $R^2$ and $R^3$ together represent methylenedioxy. Of outstanding interest are 1-n-propyl-3-(4-chlorophenyl)-xanthine,
1-n-propyl-3-(3,4-dicholorophenyl)-xanthine,
1-n-butyl-3-(3-nitrophenyl)-xanthine,
1-n-butyl-3-(3-methoxyphenyl)-xanthine, and
1-n-hexyl-3-(3,4-methylenedioxy phenyl)-xanthine.

According to a further feature of the present invention, the xanthine derivatives of general formula I can be prepared from the corresponding 6-aminouracil of the general formula:

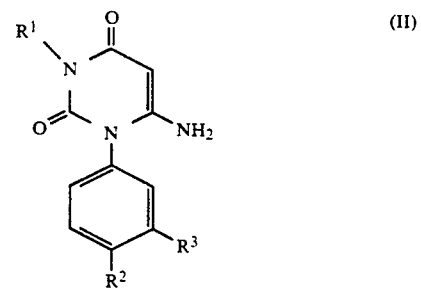

(wherein R1, R2 and R3 are as hereinbefore defined) by nitrosation, preferably with sodium nitrite and formic acid in an excess of formamide, preferably at a temperature of 40° C. to 80° C. In the reaction, the corresponding 5-nitroso derivative of general formula III is first formed in the reaction mixture:

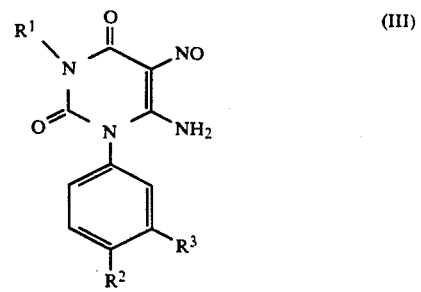

(wherein R1, R2 and R3 are as hereinbefore defined). A reducing agent such as sodium dithionite is then slowly added to the reaction mixture, preferably at a temperature of 90° C. to 120° C. This reduces the 5-nitroso group to give the corresponding 5,6-diamino derivative of general formula IV:

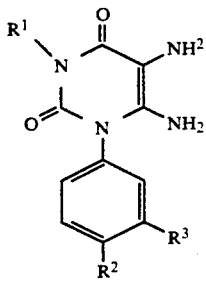

(wherein R1, R2 and R3 are as hereinbefore defined) which afterwards reacts with the formamide, usually at a temperature of 170° C. to 190° C. to give the xanthine derivative of general formula I which is then isolated in manner known per se.

By the term "methods known per se" as used in this specification and accompanying claims is meant methods heretofore or used or described in the literature.

An excess of formic acid must be used in the reaction with the 6-aminouracil derivative II and sodium nitrite, and preferably, at least two moles of formic acid are employed per mole of 6-aminouracil derivative.

Although componds III and IV that are succesively formed during the process can be isolated, the preparation of xanthine derivatives of general formula I is prefereably carried out in a single step without isolation of the intermediate compounds III and IV.

The 6-aminouracil derivatives of general formula II can be prepared from the corresponding N,N'-disubstituted urea by methods known per se, e.g. V. Papesch and E. F. Schroeder, J. Org. Chem., 16 1879-90 (1951).

The xanthine derivatives of general formula I obtained by the processes described above, can be purified by application of methods known per se, for example by recrystallization from an organic solvent, e.g. methanol, ethanol, isopropanol, tetrahydrofuran, dioxan or ethyl acetate.

The xanthine derivatives of general formula I may be converted into pharmacologically-acceptable salts with alkali metals or nitrogen-containing organic bases whose salts are formed by reaction of the compounds of general formula I with an alkali metal hydroxide or a nitrogen containing organic base using, for example, water, methanol or ethanol as a solvent at a temperature between 40° and 100° C.

The test used to detect PDE IV inhibitory potency and selectivity is based on observations reported by Gristwood and Owen (Effects of rolipram on guinea-pig ventricles in vitro: Evidence of an unexpected synergism with SK&F 94120. Br. J. Pharmacol., 87, 91P., 1985) that in isolated guinea-pig ventricles, selective PDE III inhibitors (e.g. SK&F 94120) produce a positive inotropic response whereas selective PDE IV inhibitors (e.g. rolipram) have no effect. There is, however, a synergistic interaction between selective PDE III and PDE IV inhibitors in guinea-pig ventricle. Pretreatment of guinea-pig ventricle with a concentration of a PDE III inhibitor (e.g. amrinone) will thus sensitise the preparation to PDE IV inhibitors which, when subsequently administered, will produce a positive inotropic response.

The test proceedure is as follows: male guinea-pigs of weight 400-600 g were killed, their hearts were removed and 2 ventricular preparations (ca 1 cm × 1 mm) cut from the right side. There were then mounted in organ baths containing modified Krebs-Henseleit solution of the following composition (mM): NaCl 118; NaHCO3 25; Glucose 11; KCl 5.4; CaCl2 2.5; NaH2PO4 1.2 and MgCl2 0.8.

The physiological buffer was maintained at 37° C. and continually aerated with 95% O2 / 5% CO2 v/v. The preparations were placed under 1 g resting tension and electrically stimulated to contract at 1 Hz whilst force of contraction was measured using an isometric force transducer.

Preparations were equilibrated for 60 minutes during which they were washed every 15 minutes with fresh buffer.

A concentration of a selective PDE III inhibitor (e.g. amrinone) (producing about a 100% increase in developed tension) was then added to the organ bath of one preparation in order to sensitize it to PDE IV inhibitors. The other was left untreated (to detect PDE III inhibitory activity) and 10 minutes later compounds under test were added to the organ baths in increasing concentrations and responses in both preparations measured as percentage increases in developed tension. Concentrations causing a 50% increase (EC50) were calculated.

TABLE 1

| Compound | Guinea-Pig Non-Sensitized right ventricle strips ($EC_{50\mu}M$) | Guinea-Pig Sensitized right ventricle strips ($EC_{50\mu}M$) |
| --- | --- | --- |
| THEOPHYLLINE | 1000 | 1516 |
| A | >100 | 8.9 |
| B | >100 | 7 |
| 1 | >100 | 1.6 |
| 2 | >100 | 0.1 |
| 5 | >100 | 0.9 |
| 9 | >100 | 0.2 |
| 10 | >100 | 0.4 |
| 12 | >100 | 1.3 |
| 18 | >100 | 0.2 |
| 20 | >100 | 0.3 |
| 21 | >100 | 1.2 |
| 36 | >100 | 1 |

*See structures in Table 2
Compound A is 1-methyl-3-phenylxanthine, a known compound.
Compound B is 1-propyl-3-phenyl-8-methylxanthine, a known compound.

As can be seen in Table 1 the new xanthine derivatives of the present invention are more active and selective for PDE IV relative to PDE III than the xanthine derivative in which R1 and R3 are methyl groups (i.e. theophylline) and are more active for PDE IV than the derivatives in which R3 is an unsubstituted phenyl group (compounds A and B).

The compounds of this invention are bronchodilators and have anti-inflammatory and anti-allergic activities and are therefore of use in combatting allergic/inflammatory diseases such as asthma (reversible obstructure airways disease).

The compounds of this invention also have vasodilator activity and are therefore of value in combatting angina, hypertension, congestive heart failure and multi infarct dementia. In addition the compounds are of use in combatting such other conditions wherein inhibition of PDE type IV is thought to be beneficial, such as depression, impaired cognition, rheumatic and other inflammatory diseases, stroke, heterograft rejection and other immune related diseases.

Also included within the scope of the present invention are pharmaceutical compositions which comprise, as active ingredient, at least one compound of general formula I, or a pharmacologically-acceptable salt thereof as hereinbefore mentioned, in association with a pharmaceutically acceptable carrier or diluent. Preferably the compositions are made up in a form suitable for oral, aerosol, rectal or parenteral administration.

The pharmaceutically-acceptable carriers or diluents which are admixed with the active compound or compounds or salts of such compounds to form the compositions of this invention are well known per se and the actual excipients used depend inter alia on the intended method of administration of the compositions. Compositions of this invention are preferably adapted for administration per os. In this case, the compositions for oral administration may take the form of tablets, capsules, lozenges or effervescent granules or liquid preparations such as a elixirs, syrups or suspensions, all containing one or more compounds of the invention, such preparations may be made by methods well known in the art.

The diluents which may be used in the preparation of the compositions include those liquid and solid diluents which are compatible with the active ingredient, together with colouring of flavouring agents if desired. Tablets or capsules may conveniently contain between 1 and 50 mg and preferably from 5 to 30 mg of active ingredient or the equivalent amount of a pharmacologically-acceptable salt thereof. The compounds may also be incorporated into pellets coated with appropiate natural or synthetic polymers known in the art to produce sustained release characteristics or incorporated with polymers into tablet form to produce the same characteristics.

The liquid compositions adapted for oral use may be in the form of solutions, suspensions or aerosols. The solutions may be aqueous or aqueous-alcoholic solutions of a soluble compound or salt thereof in association with, for example, sucrose or sorbitol to form a syrup. The suspensions may comprise an insoluble or microencapsulated form of an active compound of the invention in association with water and other acceptable solvents together with a suspending agent or flavouring agent.

Compositions for oral aerosol administration may be in the form of solutions, suspensions or micronized powder, contained in an appropiate inhaler.

Compositions for parenteral injection may be prepared from soluble compounds or salts, which may or may not be freeze-dried and which may be dissolved in water or an appropriate parenteral injection fluid.

In human therapy, the doses of the xanthine derivatives depend on the desired effect and duration of the treatment; adult doses are generally between 1 mg and 100 mg per day. In general the physician will decide the posology taking into account the age and weight intrinsic to the patient being treated.

The following examples illustrate the invention.

EXAMPLE 1

A mixture of 1-(4-chlorophenyl)-3-n-propyl-6-aminouracil (28.0 g; 0.1 mole), formic acid (15.1 ml; 0.4 moles) and sodium nitrite (7 g; 0.1 mole) in formamide (600 ml) was heated to 60° C. for 10 minutes. The temperature was then increased to 100° C. and sodium dithionite (2.3 g; 0.013 moles) was added over a period of 10 minutes. After addition, the temperature was increased to 190° C., mantained for 30 minutes and the reaction mixture was cooled and extracted with chloroform. The organic solution was extracted with 2N sodium hydroxide aqueous solution, washed with diethyl ether, acidified with 2N hydrochloric acid aqueous solution and extracted with chloroform. The organic extracts were washed with water, dried (Na2SO4) and the solvent was removed in vacuo to give 1-n-propyl-3-(4-chlorophenyl)-xanthine (19.5 g; yield 64.3%). After recrystallization from 90% ethanol, the melting point is 233°-234° C.

The xanthine derivatives of general formula I included in Table 2 were prepared according to the process disclosed in this example 1 but with appropriate substitution on the 6-amino uracil reactant.

TABLE 2

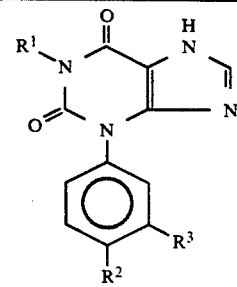

| Comp. Nr. | R$^1$ | R$^2$ | R$^3$ | Melting Point °C. |
|---|---|---|---|---|
| 1 | nC$_3$H$_7$ | Cl | H | 233-234 |
| 2 | " | H | Cl | 196-198 |
| 3 | " | F | H | 258-259 |
| 4 | " | H | F | 213-214 |
| 5 | " | Br | H | 228-229 |
| 6 | " | CH$_3$ | " | 227-229 |
| 8 | " | OCH$_3$ | H | 203-205 |
| 9 | " | H | OCH$_3$ | 203-205 |
| 10 | " | " | NO$_2$ | 224-228 |
| 11 | " | " | CF$_3$ | 159-161 |
| 12 | " | Cl | Cl | 231-232 |
| 13 | " | F | F | 231-232 |
| 14 | " | OCH$_3$ | OCH$_3$ | 248-249 |
| 15 | " | " | Cl | 266-268 |
| 16 | n-C$_4$H$_9$ | Cl | H | 197-198 |
| 17 | " | H | Cl | 191-192 |
| 18 | " | F | H | 246-248 |
| 19 | " | H | F | 172-173 |
| 20 | " | OCH$_3$ | H | 197-200 |
| 21 | " | H | OCH$_3$ | 189-190 |
| 22 | " | " | NO$_2$ | 177-180 |
| 23 | " | Cl | Cl | 206-208 |
| 24 | " | H | CF$_3$ | 167-168 |
| 25 | nC$_5$H$_{11}$ | Cl | H | 180-183 |
| 26 | " | " | Cl | 211-212 |
| 27 | nC$_6$H$_{13}$ | " | Cl | 161-163 |
| 28 | " | " | Cl | 190-191(d) |
| 29 | iC$_4$H$_9$ | " | H | 218-219 |
| 30 | " | " | Cl | 218-219 |
| 31 | CH$_2$—CH=CH$_2$ | " | H | 242-244 |
| 32 | CH$_2$—C≡CH | " | " | 261-262 |
| 33 | n-C$_3$H$_7$ | O—CH$_2$—O | | 225-227 |
| 34 | n-C$_4$H$_9$ | O—CH$_2$—O | | 214-216 |
| 35 | n-C$_5$H$_{11}$ | " | | 218-219 |
| 36 | n-C$_6$H$_{13}$ | " | | 167-169 |
| 37 | i-C$_4$H$_9$ | " | | 247-248 |
| 38 | n-C$_3$H$_7$ | O—CH$_2$CH$_2$—O | | 222-223 |
| 39 | n-C$_4$H$_9$ | " | | 180-181 |

The following Examples illustrate pharmaceutical compositions according the invention.

EXAMPLE 2

100,000 capsules each containing 20 mg of 1-n-propyl-3-(4-chloro- or 3,4-dichlorophenyl)-xanthine (active ingredient) were prepared from the following formulation:

| | |
|---|---|
| 1-n-propyl-3-(4-chloro- or 3,4-dichlorophenyl)-xanthine | 2 kg |
| Lactose monohydrate | 11.7 kg |
| Corn starch | 1 kg |
| Colloidal silicon dioxide | 0.1 kg |

PROCEDURE

The above ingredients were sieved through a 60-mesh sieve, then mixed in a suitable mixer and filled into 100,000 gelatine capsules.

EXAMPLE 3

1000 bottles of suspension (capacity 150 ml) each containing 150 mg of 1-n-butyl-3-(3-nitrophenyl)-xanthine were prepared as follows:

| | |
|---|---|
| 1-n-butyl-3-(3-nitrophenyl)-xanthine | 150 g |
| microcrystalline cellulose | 1,500 g |
| sodium carboxymethycellulose | 900 g |
| 70% sorbitol aqueous solution | 33,000 g |
| glycerine | 4,500 g |
| polysorbate 80 | 400 g |
| sodium methyl p-hydroxybenzoate | 240 g |
| sodium propyl p-hydroxybenzoate | 60 g |
| anti-foam silicone | 150 g |
| sodium saccharin | 300 g |
| flavouring q.s. | |
| demineralised water q.s. | 150 liters |

PROCEDURE

To a solution of the sodium methyl p-hydroxybenzoate, sodium propyl p-hydroxybenzoate and sodium saccharin in 30 litres of demineralised water, a wetmilled suspension of the sodium carboxymethycellulose in glycerine was added. After stirring for 1 hour, a suspension of the microcrystalline cellulose in 60 liters of demineralised water was added and then the sorbitol solution, polysorbate 80, 1-n-butyl-3-(3-nitrophenyl)-xanthine and flavouring 80, 1-n-butyl-3-(3-nitrophenyl)-xanthine and flavouring were successively added with stirring. The volume of the mixture was adjusted to 125 litres with demineralised water and milled through a colloidal mill. Antifoam silicone was added and the suspension made up to volume with demineralised water and filled into 150 ml bottles using an appropiate filling machine.

EXAMPLE 4

20,000 bottles of solution (capacity 150 ml) each containing 150 mg of 1-n-butyl-3-(3-methoxyphenyl)-xanthine were prepared as follows:

| | |
|---|---|
| 1-n-butyl-3-(3-methoxyphenyl)-xanthine | 3 kg |
| ethanol | 45 kg |
| 70% sorbitol aqueous solution | 1,050 kg |
| sodium saccharin | 3 kg |
| sodium carboxymethylcellulose | 60 kg |
| flavouring q.s. | |
| demineralised water q.s. | 3,000 liters |

PROCEDURE

A solution of the sodium carboxymethylcellulose in 1,000 litres of water and 5 kg of ethanol was added to another solution of the I-n-butyl-3-(3-methoxyphenyl)-xanthine in 40 kg of ethanol and 500 litres of water at a temperature of 50° C. Then the sorbitol solution, sodium saccharin and flavouring were added and the volume of the mixture was adjusted to 3,000 liters with demineralised water. After filtration, the solution was filled into 150 ml bottles using an appropiate filling machine.

EXAMPLE 5

10,000 Suppositories each containing 50 mg of 1-n-hexyl-3-(3,4-methylenedioxyphenyl)-xanthine were prepared as follows:

| | |
|---|---|
| 1-n-hexyl-3-(3,4-methylenedioxyphenyl)-xanthine | 500 g |
| theobroma oil | 19,500 g |

The theobroma oil was melted and the active compound suspended in it. The mixture was then poured into appropiate suppository mould to make 2.0 g suppositories.

EXAMPLE 6

8,000 Inhalation-flasks each containing 100 mg of 1-n-hexyl-3-(3,4-methylenedioxyphenyl)-xanthine (active compound) were prepared as follows:

| | |
|---|---|
| 1-n-hexyl-3-(3,4-methylenedioxyphenyl)-xanthine | 800 g |
| sorbitan trioleate | 8 g |
| water q.s. | 160 liters |
| nitrogen q.s. to a pressure of 7-8 kg/cm$^2$ | |

The microcrystalline suspension prepared with these ingredients was introduced in the inhalation-flasks at a volume of 20 ml per flask with a filling machine at a nitrogen pressure of 7-8 kg/cm$^2$. The flasks are furnished with an appropiate valve which releases 0.2 ml of suspension in each activation (1 mg of active compound).

We claim:

1. A compound of the formula:

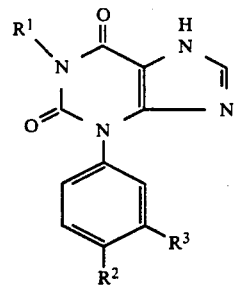

wherein $R^1$ represents a straight or branched chain alkyl, alkenyl or alkynyl group 3-6 carbon atoms, and $R^2$ and $R^3$, which may be the same or different, each represent hydrogen or halogen or a methyl, methoxy, nitro or trifluoromethyl group or $R^2$ and $R^3$ together form a methylenedioxy or ethylenedioxy group; with the proviso that $R^2$ and $R^3$ are not both hydrogen; and pharmacologically acceptable salts thereof with an alkali metal base or a nitrogen containing organic base.

2. A compound according to claim 1 wherein $R^1$ is an n-propyl, iso-propyl, n-butyl, iso-butyl, tert.butyl or n-hexyl group.

3. A compound according to claim 1 wherein $R^2$ and $R^3$, which may be the same or different, each represent H, F, Cl, Br, or methoxy or $R^2$ and $R^3$ together represent methylenedioxy.

4. A compound according to claim 1 which is
1-n-propyl-3-(4-chlorophenyl)-xanthine,
1-n-propyl-3-(3,4-dichlorophenyl)-xanthine,
1-n-butyl-3-(3-nitrophenyl)-xanthine,
1-n-butyl-3-(3-methoxyphenyl)-xanthine,
or 1-n-hexyl-3-(3,4-methylenedioxyphenyl)-xanthine.

5. A method for inhibiting type IV phosphodiesterase in animals, including man, comprising administering to a host in need of such treatment an effective amount of a xanthine of formula I as defined in claim 1.

6. A pharmaceutical preparation comprising as active ingredient an effective amount of a compound of the formula I or a salt thereof as defined in claim 1 in association with a pharmaceutically acceptable carrier or diluent.

7. A method for the treatment of allergic and inflammatory diseases in animals, including man, characterised by administering to a host in need of such treatment an effective amount of a compound of the formula I or a salt thereof as defined in claim 1.

8. A pharmaceutical composition comprising a xanthine of the formula I or salt thereof as defined in claim 1 together with a pharmaceutically acceptable carrier or diluent.

9. A compound of the formula:

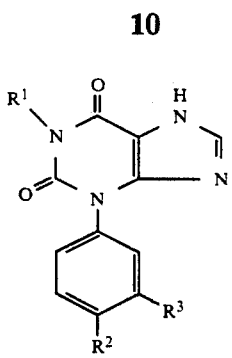

wherein $R^1$ represents a straight or branched chain alkyl, alkenyl or alkynyl group of 3-6 carbon atoms, and $R^2$ and $R^3$, which may be the same or different, each represent hydrogen or halogen or a methyl, methoxy, nitro or trifluoromethyl group or $R^2$ and $R^3$ together form a methylenedioxy or ethylenedioxy group; with the proviso that $R^2$ and $R^3$ are not both hydrogen; and pharmacologically acceptable salts thereof with an alkali metal base or a nitrogen base containing organic base, prepared by the process of reacting a 5,6-diamine of the formula:

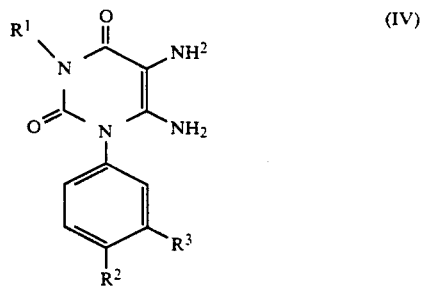

where $R^1$, $R^2$ and $R^3$ are as defined above, with formamide, and recovering said compound of the formula I.

* * * * *